United States Patent [19]
Ojo et al.

[11] Patent Number: 5,618,818
[45] Date of Patent: Apr. 8, 1997

[54] MUSCARINIC AGONIST COMPOUNDS

[75] Inventors: Babatunde Ojo, Richmond, Va.; Philip G. Dunbar, Medical Lake, Wash.

[73] Assignee: The University of Toledo, Toledo, Ohio

[21] Appl. No.: 618,986

[22] Filed: Mar. 20, 1996

[51] Int. Cl.$^6$ .................... A61K 31/505; C07D 239/06; C07D 239/14
[52] U.S. Cl. .................... 514/256; 544/332; 544/335; 514/275
[58] Field of Search .................... 544/335, 332; 514/256, 275

[56]  References Cited

U.S. PATENT DOCUMENTS

| | | | |
|---|---|---|---|
| 4,710,508 | 12/1987 | Bergmeier et al. | 514/357 |
| 4,786,648 | 11/1988 | Bergmeier et al. | 514/357 |
| 5,175,166 | 12/1992 | Dunbar et al. | 514/275 |
| 5,403,845 | 4/1995 | Dunbar et al. | 514/257 |

OTHER PUBLICATIONS

J. Med. Chem. 1990, 33, 1128–1138 Saunders J. et. al.
J. Med. Chem. 1990, 33, 2052–2059 MacLeod. et al.
J. Med. Chem. 1991, 34, 687–692 Per Sauerberg et al.

*Primary Examiner*—Mukund J. Shah
*Assistant Examiner*—Sabiha N. Qazi
*Attorney, Agent, or Firm*—Brinks Hofer Gilson & Lione

[57] ABSTRACT

A muscarinic agonist compound having the structure (I) or (II):

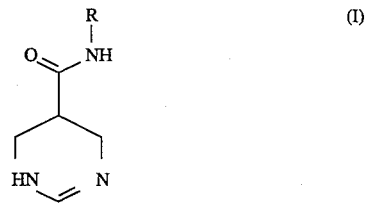

where R is methyl or dimethylamino; or

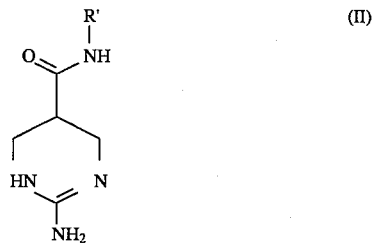

where R' is dimethylamino.

5 Claims, No Drawings

MUSCARINIC AGONIST COMPOUNDS

The present invention relates to amidine derivative compounds having binding affinities and/or agonist activity at muscarinic receptors in the central nervous system.

BACKGROUND OF THE INVENTION

The University of Toledo U.S. Pat. Nos. 5,175,166 and 5,403,845 (Dunbar, Durant, Hoss and Messer) disclose muscarinic agonists and are hereby incorporated by reference. As stated therein, there is a need in the art to provide muscarinic agonists which have activity at various muscarinic receptors subtypes in the central nervous system.

OBJECTS OF THE INVENTION

It is an object of the present invention to satisfy the above need in the art with amidine derivative compounds hereinafter disclosed.

It is an object of the present invention to provide a compound having the formula (I) or (II) below or a pharmaceutically acceptable salt thereof:

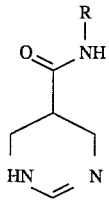
(I)

where R is methyl or dimethylamino; or

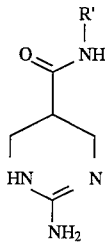
(II)

where R' is dimethylamino.

It is an object of the present invention to provide a pharmaceutical preparation effective for stimulating a muscarinic receptor and also to provide a method for providing a therapeutic benefit to a mammal by administering to the mammal the above described certain amidine derivative muscarinic agonist compounds.

These and other objects will be apparent from the specification that follows and the appended claims.

SUMMARY OF THE INVENTION

The present invention provides a compound having the formula (I) or (II) below or a pharmaceutically acceptable salt thereof:

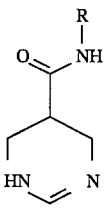
(I)

where R is methyl or dimethylamino; or

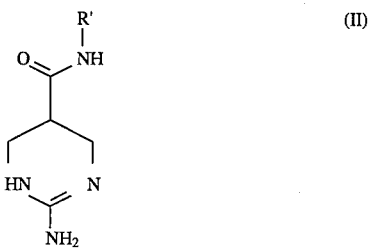
(II)

where R' is dimethylamimo.

The invention also provides a pharmaceutical preparation effective for stimulating a muscarinic receptor, comprising the above stated compounds, or a pharmaceutically acceptable salt thereof, together with a pharmaceutically acceptable solid or liquid carrier.

The present invention also provides a method of providing a therapeutic benefit to a mammal comprising administering to said mammal a drug in effective amounts to stimulate a muscarinic receptor so as to provide such benefit, the improvement wherein said drug is a compound as above described or its pharmaceutical salt.

DETAILED DESCRIPTION OF THE INVENTION

In the aforementioned U.S. Pat. No. 5,175,166 in column 32, Table 1 shows test results of 15 compounds including some muscarinic agonists. In commenting upon the results, in column 33, two sentences in lines 3–7 state as follows:

Thus the unpredictable nature of this technology will be readily apparent. Changing a hydrogen atom (Ex. 10) to a methyl group (Ex. 19) resulted in the production of an inactive and unacceptable composition.

Surprisingly, in the present invention, the disclosed amidine derivatives show unusual and excellent results as illustrated in Table 1 that follows herein.

TABLE 1

Binding affinities and agonist activity in a series of amidine derivatives at muscarinic receptors in the rat central nervous system. Data represent the mean from one to three experiments, each performed in triplicate.

| Chemical Structure | Functionality | Ligand | $IC_{50}$ $[^3H]$-QNB | PI cortex (at 100 μM) |
|---|---|---|---|---|
| | R = methyl | CDD-0131-A | 54 μM | 120 |
| | dimethylamino | CDD-0125--A | 3.7 μM | 160 |

TABLE 1-continued

Binding affinities and agonist activity in a series of amidine derivatives at muscarinic receptors in the rat central nervous system. Data represent the mean from one to three experiments, each performed in triplicate.

| Chemical Structure | Functionality | Ligand | IC$_{50}$ [$^3$H]-QNB | PI cortex (at 100 μM) |
|---|---|---|---|---|
| (structure) | R' R = dimethylamino | CDD-0126-A | 50 μM | 58% |

The following examples illustrate the preparation of the superior and unusual muscarinic agonist compounds.

EXAMPLE 1

1,4,5,6-tetrahydropyrimidine-5-carboxylic-N-methylamide HCl (10)

1,4,5,6-tetrahydropyrimidine-5-carboxylic acid hydrochloride (0.5 g, 3.1 mmol) was suspended in a solution of oxalyl chloride (0.7 mL, 7.6 mmol) in benzene (10 mL), heated with stirring under reflux for 2.5 h, and then evaporated to dryness in vacuo after cooling, to give an orange-yellow residue. The last traces of oxalyl chloride were removed by adding 10 mL of benzene to the residue, then the residue was evaporated to dryness in vacuo to give an orange residue of the crude acid chloride (0.6 g). The residue was suspended in dry dichloromethane (20 mL) under a nitrogen atmosphere. Methylamine hydrochloride (6.1 mmol) and DBU (1,8-diazabicyclo[5.4.0]undec-7-ene) 98% (0.9 mL, 6.1 mmol) were added, and the mixture was stirred at 20° C. for 16 h. The mixture was taken up in aqueous K$_2$CO$_3$ (2M, 50 mL), extracted (3×200 mL) with dichloromethane and the extracts were dried (MgSO$_4$). The extracts were combined and evaporated to dryness in vacuo to give a pale-yellow residue. The hydrochloride salt was obtained by addition of 1M HCl in ether to an ethanol solution of the residue, evaporation of solvents to dryness in vacuo and recrystallization (ethanol/ether) to give crystals (0.7 g, 62%) of 1,4,5,6-tetrahydropyrimidine-5-carboxylic-N-methylamide as the hydrochloride salt: mp 150°–151° C.; $^1$H NMR (D$_2$O): δ2.4 (D,3H), 2.80 (q, 1H), 3.09 (m, 1H), 3.5 (d, 4H), 7.8 (s, 1H). Anal. (C$_6$H$_{12}$N$_3$OCl) C, H, N.

EXAMPLE 2

1,4,5,6-tetrahydopyrimidine-5-carboxylic hydrazide HCl (11)

1,4,5,6-tetrahydopyrimidine-5-carboxylic acid hydrochloride (1.1 g, 6.2 mmol) and thionyl chloride (0.3 mL, 1.4 mmol) were refluxed in anhydrous methanol (50 mL) for 24 h. Evaporation of solvents to dryness in vacuo gave a white residue of the:methyl ester (1.1 g, 96%). The methyl ester, dissolved in hydrazine monohydrate 98% (0.8 mL, 16.6 mmol), was refluxed in methanol (20 mL) for 2 h, and then evaporated to:dryness in vacuo to give a pink residue. Recrystallization of the residue from methanol and diethyl ether gave crystals (0.3 g, 49%) of 1,4,5,6-tetrahydropyrimidine-5-carboxylic hydrazide as the hydrochloride salt: $^1$H NMR (CD$_3$OD): δ2.7 (m, 1H) 3.0 (m, 1H), 3.5 (d, 4H), 5.85–6.04 (br d, 2H, NH$_2$), 7.9 (s, 1H); MS m/z 142 (M$^+$ of free base). Anal. (C$_5$H$_{11}$N$_4$OCl) C, H, N.

1,4,5,6-tetrahydropyrimidine-5-carboxylic-(N,N-dimethyl)hydrazide HCl (12)

5-(Methyloxycarbonyl)-1,4,5,6-tetrahydropyrimidine hydrochloride (0.5 g, 2.8 mmol) and N,N-dimethylhydrazine 98% (1.0 mL, 13.2 mmol) were refluxed in anhydrous methanol (20 mL) for 2 h, and then evaporated to dryness in vacuo to give a yellow residue. Recrystallization of the residue from absolute ethanol and diethyl ether yielded crystals (0.3 g, 51%) of 1,4,5,6-tetrahydropyrimidine-5-carboxylic-(N,N-dimethyl)hydrazide as the hydrochloride salt: mp 180°–181° C.; $^1$H NMR (D$_2$O): δ2.8 (s, 1H), 3.1 (m, 1H), 3.5 (d, 4H), 3.7 (s, 6H), 7.8 (s, 1H); MS m/z 180 (M$^+$ of free base). Anal. (C$_7$H$_{15}$N$_4$OCl) C, H, N.

EXAMPLE 3

2-Amino-1,4,5,6-tetrahydropyrimidine-5-carboxylic-(N,N-dimethyl)hydrazide HCl (16)

2-Amino-1,4,5,6-tetrahydropyrimidine-5-carboxylic acid (0.1 g, 0.5 mmol) and thionyl chloride (0.2 mL, 1.4 mmol) were refluxed in methanol for 24 h, and then evaporated to dryness in vacuo to give 2-amino-5-methyloxycarbonyl-1,4,5,6-tetrahydropyrimidine hydrochloride. 2-Amino-5-methyloxycarbonyl-1,4,5,6-tetrahydropyrimidine hydrochloride (0.1 g, 0.6 mmol) and N,N-dimethylhydrazine 98% (0.4 mL, 5.3 mmol) were refluxed in anhydrous methanol (20 mL) for 2 h, then evaporated to dryness in vacuo to give a white residue. Recrystallization of the residue from absolute ethanol and diethyl ether gave crystals (40 mg, 58%) of 2-amino-1,4,5,6-tetrahydropyrimidine-5-carboxylic-(N,N-dimethyl)hydrazide as the hydrochloride salt: mp 192°–193° C.; $^1$H NMR (D$_2$O): δ2.8 (s, 1H), 3.0 (m, 1H), 3.50 (d, 4H), 3.65 (s, 6H); MS m/z 156 (M$^+$ of free base). Anal. (C$_7$H$_{16}$N$_5$OCl) C, H, N.

In the case of Example 3, the compound is made according to Scheme 10.

Scheme 10

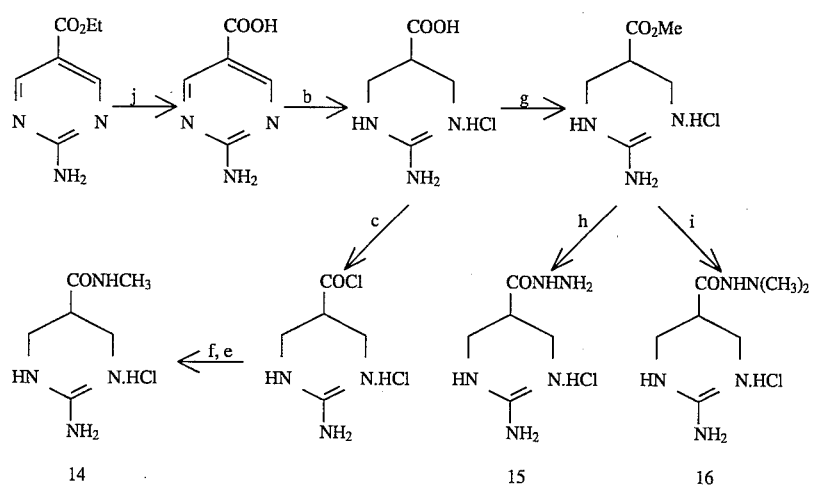

Reaction Conditions: j = KOH, MeOH, reflux., b = $H_2$, Pd-on-Carbon (10%), aq. HCl., c = oxalyl chloride solution in benzene, reflux., e = ethereal HCl (1 M)., f = methylamine, $CH_2Cl_2$, triethylamine., g = $SOCl_2$, MeOH, reflux., h = hydrazine, MeOH, reflux., i = N,N-dimethylhydrazine, MeOH, reflux.

The compounds of Examples 1 and 2 are made according to Scheme 9 (see compounds 10 and 11).

Scheme 9

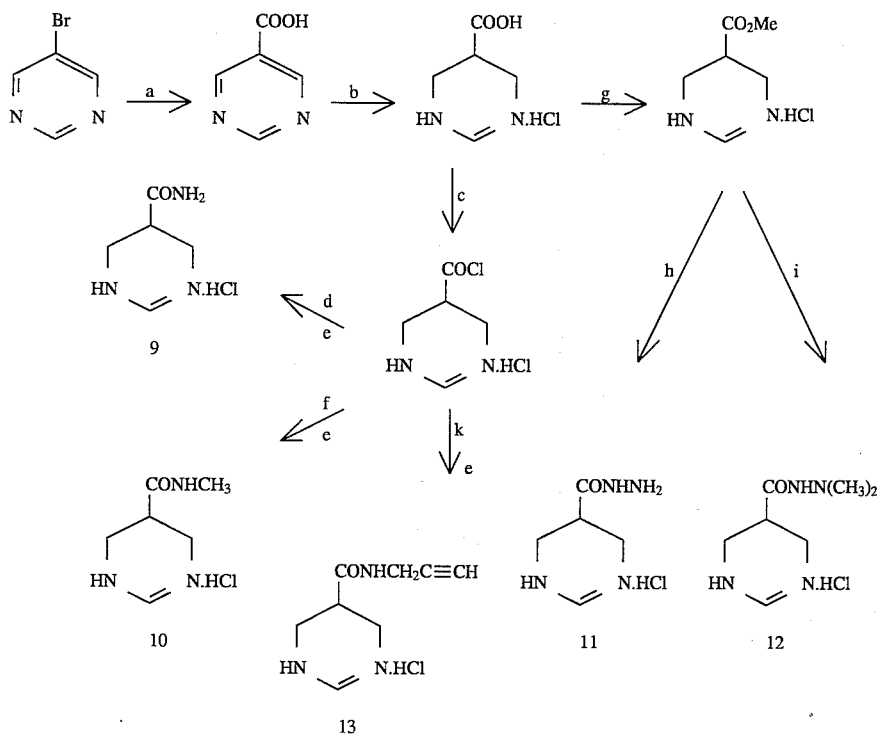

Reaction Conditions: a = n-BuLi, $CO_2$., b = $H_2$, Pd-on-Carbon (10%), aq. HCl., c = oxalyl chloride solution in benzene, reflux., d = $NH_3$, $CH_2Cl_2$, triethylamine., e = ethereal HCl (1 M)., f = methylamine, $CH_2Cl_2$, triethylamine., g = $SOCl_2$, MeOH, reflux., h = hydrazine, MeOH, reflux., i = N,N-dimethylhydrazine, MeOH, reflux., k = propargylamine, $CH_2Cl_2$, triethylamine, ethereal HCl (1 M)-add

What is claimed is:

1. A compound having the formula (I) or (II) below or a pharmaceutically acceptable salt thereof:

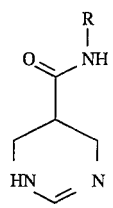  (I)

where R is methyl or dimethylamino; or

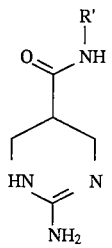  (II)

where R' is dimethylamino.

2. A compound as defined in claim 1 in which R is methyl.

3. A compound as defined in claim 1 in which R is dimethylamino.

4. A pharmaceutical preparation effective for stimulating a muscarinic receptor, comprising a compound of claim 1, or a pharmaceutically acceptable salt thereof, together with a pharmaceutically acceptable solid or liquid carrier.

5. In a method of providing a therapeutic benefit to a mammal comprising administering to said mammal a drug in effective amounts to stimulate a muscarinic receptor so as to provide such benefit, the improvement where in said drug is a compound of claim 1 or its pharmaceutically acceptable salt.

* * * * *